United States Patent
Pavliv et al.

(10) Patent No.: US 8,778,907 B2
(45) Date of Patent: Jul. 15, 2014

(54) LACTULOSE FOR BOWEL EVACUATION

(75) Inventors: Leo Pavliv, Cary, NC (US); Bryan Voss, Nashville, TN (US)

(73) Assignee: Cumberland Pharmaceuticals, Nashville, TN (US)

( * ) Notice: Subject to any disclaimer, the term of this patent is extended or adjusted under 35 U.S.C. 154(b) by 51 days.

(21) Appl. No.: 13/284,332

(22) Filed: Oct. 28, 2011

(65) Prior Publication Data

US 2012/0277181 A1 Nov. 1, 2012

Related U.S. Application Data

(60) Provisional application No. 61/479,651, filed on Apr. 27, 2011.

(51) Int. Cl.
*A61K 31/70* (2006.01)
(52) U.S. Cl.
USPC .......................................................... 514/53
(58) Field of Classification Search
USPC .......................................................... 514/53
See application file for complete search history.

(56) References Cited

U.S. PATENT DOCUMENTS

| | | | |
|---|---|---|---|
| 7,687,075 B2 | 3/2010 | Skiendzielewski et al. |
| 7,718,197 B2 | 5/2010 | Skiendzielewski et al. |
| 2005/0271749 A1 | 12/2005 | Borody et al. |
| 2007/0196322 A1 | 8/2007 | Pelham |
| 2012/0277181 A1 | 11/2012 | Pavliv et al. |

OTHER PUBLICATIONS

Ouyang et al. "Lactulose in Children with Bowel Preparation Before Colonoscopy in the Application,".
Ouyang et al. "Lactulose in Children with Bowel Preparation Before Colonoscopy in the Application," Chin. J. Contemp. Pediatr. vol. 12, No. 9, 2010 (English translation).
International Search Report for corresponding International Application WO2012149353 A1, dated Jul. 19, 2012.
Florie et al., "MR Colongraphy with Limited Bowel Preparation Compared with Optical Colonoscopy in Patients at Increased Risk for Colorectal Cancer," Radiology: vol. 243, No. 1, Apr. 2007; pp. 122-131.
Florie et al., "Feasibility Study of Computed Tomography Colonography Using Limited Bowel Preparation at Normal and Low-dose Levels Study" Eur. Radiol. (2007) 17: pp. 3112-3122.
Florie et al., "MR Colongraphy With Limited Bowel Preparation," Radiology vol. 245: No. 1, Oct. 2007; pp. 150-159.
Urita, et al. "Hydrogen Breath Test as an Indicator of the Quality of colonic Preparation for Colonoscopy" Gastrointestinal Endoscopy vol. 57, No. 2, 2003; pp. 174-177.
Gidwani, et al., "A Prospective Randomized Single-blind Comparison of Three mehods of Bowel Preparation for Outpatient Flexible Sigmoidoscopy", Surg Endosc (2007) 21: 945-949.

*Primary Examiner* — Elli Peselev
(74) *Attorney, Agent, or Firm* — Davidson, Davidson & Kappel, LLC

(57) ABSTRACT

A method of treating an adult patient in need of bowel evacuation via the administration of one or more doses of a bowel evacuant consisting of a total of from about 180 g to about 220 g of lactulose in a dosing regimen suitable to achieve bowel evacuation prior to a diagnostic, therapeutic or surgical procedure is disclosed.

38 Claims, No Drawings

LACTULOSE FOR BOWEL EVACUATION

BACKGROUND OF THE INVENTION

Colonoscopy is the endoscopic examination of the colon and the distal part of the small bowel with a CCD camera or a fiber optic camera on a flexible tube passed through the anus. It may provide a visualization of the colon and allows the physician to ascertain the presence of ulceration and/or polyps, and also provides the opportunity for biopsy of polyps or removal of suspected polyps/lesions. Colonoscopy is an important procedure for the screening, prevention and diagnosis of a number of diseases of the colon, especially colorectal cancer. In order to perform a useful colonoscopy, a complete evacuation of the contents of the bowel is required. In this regard, numerous purgative products have been developed for this purpose.

Adequate preparation of the colon is essential for complete colonoscopy with proper visualization of the mucosa. A great deal of effort has been devoted to improving the methods of colonic preparation. Polyethylene glycol has been used widely as a method for bowel cleansing, but leaves a significant percentage of patients receiving poorly prepared for their colonoscopy. This necessitates another bowel cleansing, and causes cancellation of the initially scheduled procedure, and in some cases cancellation of the procedure altogether by the patient.

While various methods of bowel preparation are used prior to colonoscopy, there is no general "gold standard" procedure. Useful bowel preparations are those that provide adequate visualization of the bowel with minimal patient discomfort or side effects. Most preferably, the bowel preparation must be acceptable to the patient. It should also preferably be inexpensive and easy for the patient to self-administer. In the past, both rectal and oral preparations, alone or in combination, have been used to cleanse the colon. Enemas have in the past been a preferred option because they quickly clear the bowel and require no dietary restrictions compared to oral preparations, however are not often used due to patient acceptability.

It has been established that adenomatous polyps are precursors of cancer, and that removal of these polyps can prevent colorectal cancer. For this reason, the development of screening methods for early detection of these established precursors of cancer has received increasing attention. These screening methods include computed tomographic (CT) colonography and magnetic resonance (MR) colonography.

Recent randomized trials comparing different methods of bowel preparations have considered the quality of bowel preparation as the focus of their study.

For example, Gidwani, et al., "A Prospective Randomized Single-blind Comparison of Three methods of Bowel Preparation for Outpatient Flexible Sigmoidoscopy", Surg Endosc (2007) 21: 945-949 (Abstract published in Gastrointest Endosc 2004; (59 (5): 127) reported a study concerning the performance of out-patient flexible sigmoidoscopy prospectively randomized to 3 groups: group 1: one Fleet enema 2 hours pre-procedure; group 2: two Fleet enemas, one on the evening prior to sigmoidoscopy and one 2 hours preprocedure; group 3: lactulose 30 ml orally 48 and 24 hours prior to sigmoidoscopy, plus a single Fleet enema 2 hours pre-procedure. A patient questionnaire was used to assess side effects and tolerance. There was no significant difference between the groups in terms of depth of insertion (p=0.42—chi-squared test) or abnormalities noted (p=0.34—chi-squared test). Nor was there any difference in the quality of preparation of patients in group 1 versus group 2 (p=0.39—Fishers exact test) or group 1 versus group 3 (p=0.13—Fishers exact). However, it was reported therein that lactulose+Fleet resulted in significantly fewer patients with acceptable preparation compared with those who administered two Fleet enemas (p=0.02—Fishers exact test). The authors concluded that the addition of a Fleet enema or oral lactulose over and above a single Fleet enema gives no significant improvement in the acceptability or efficacy of bowel preparation. This study further concluded that a single phosphate enema 2 hours pre-procedure is an effective method of bowel preparation for flexible sigmoidoscopy, and provides an acceptable quality of bowel preparation in approximately four of every five patients. The addition of a single phosphate enema or oral lactulose over and above this standard regimen was considered by the authors to be more costly and time consuming, and the addition of an extra enema or lactulose did not alter patient acceptability or quality of bowel preparation.

Florie, et al. "MR Colongraphy with Limited Bowel Preparation Compared with Optical Colonoscopy in Patients at Increased Risk for Colorectal Cancer" (Radiology: Volume 243, Number 1, April 2007) prospectively evaluated the diagnostic performance of magnetic resonance (MR) colonography by using limited bowel preparation in patients with polyps of 10 mm or larger in diameter in a population at increased risk for colorectal cancer, with optical colonoscopy as the reference. MR colonography was performed within 2 weeks prior to optical colonoscopy. All patients started preparation 48 hours prior to MR colonography with a low-fiber diet (only well-cooked, nonfibrous vegetables and meat, no fibrous fruit, no whole-wheat cereal products, no nuts), together with ingestion of 12 g of lactulose powder in 6-g packets (Lactulose CF; Centrafarm, Etten-Leur, the Netherlands) dissolved in water once per day (in the morning) for stool softening. An oral contrast agent that contained 10 ml of gadolinium in a dose of 0.5 mmol/ml (gadopentetate dimeglumine, Magnevist; Schering, Berlin, Germany) was added to all major meals during this period (6 meals over 2 days) for stool tagging. If the stool became too soft (diarrhea), patients were allowed to reduce the amount of lactulose. In a questionnaire, patients were asked about stool consistency prior to imaging and whether they reduced the amount of lactulose. Patients ingested 4-6 L of polyethylene glycol electrolyte solution (KleanPrep; Helsinn Birex Pharmaceuticals, Dublin, Ireland) for bowel preparation on the day before the examination (in patients who ingested 6 L, the last 2 L of that amount was ingested on the examination day). Optical colonoscopy was used as the reference standard. Optical colonoscopy was performed with a standard colonoscope. Of the 168 patients, 77 (38%) of the patients had diarrhea sometime during the bowel preparation; in 48 of these patients, diarrhea occurred just prior to imaging. Thirty seven patients reduced the amount of lactulose (all but one did so only on the last day). Prior to imaging in 191 patients, a spasmolytic agent was administered. One hundred forty-nine patients received butylscopo-lamine bromide, 42 received glucagon, and nine received no spasmolytic agent. On average, 1.9 L of water-gadolinium mixture was used to fill the colon. Two patients had considerable leakage; in 11, leakage was minor. MR colonography was well tolerated.

Florie, et al., "Feasibility Study of Computed Tomography Colonography Using Limited Bowel Preparation at Normal and Low-dose Levels Study" (Eur Radiol (2007) 17: 3112-3122) evaluated limited bowel preparation computed tomography colonography (CTC) using an oral contrast agent (amidotrizoic acid) in terms of image quality, patient acceptance and polyp visualization using conventional colonoscopy as a reference standard. Four weeks prior to the conventional colonoscopy, patients were asked to ingest amidotrizoic acid (20 mg/ml, made by the hospital pharmacy, 11.7 mg I/ml; corresponding to approximately 30 times diluted Gastrografin370®) three times a day (100 ml at breakfast and lunch, 300 ml at dinner) with a low-fiber diet (well cooked vegetables and meat, no fibrous fruit, no whole-wheat products, no nuts) starting 2 days prior to CTC. Lactulose (12 g, lactulose CF powder 6 g/sachet, Centrafarm, Etten-Leur, The Netherlands) was taken in the morning for 3 days prior to CTC for stool softening. Twenty mg of butylscopolaminebromide (Buscopan; Boehringer-Ingelheim, Ingelheim, Germany), when contraindicated, 1 mg of glucagon hydrochloride (Glucagen; Novo-Nordisk, Bagsvaerd, Denmark) was administered intravenously. The colon was insufflated with a $CO_2$-air mixture (13.2% vol.) using a flexible catheter until patients experienced discomfort (±2-3 l). Patients were scanned in prone and supine position with a four-sliceMX8000 (PhilipsMedical Systems, Best, The Netherlands) CT scanner (120 kV, rotation time 0.75 s, pitch 1.25, collimation 4.*2.5 mm, section thickness 3.2 mm, and reconstruction interval 1.6 mm, 50 or 70 milliampere-second (mAs); 70 mAs if the abdominal circumference was >102.5 cm, scan time 20-25 s). Prior to CC, each patient was instructed to ingest 4 l of a macrogol solution (Colofort macrogol 4000 sachets, Ipsen, Hoofddorp, The Netherlands), starting on the evening prior to the CC. The authors took the position that the study demonstrated that CTC without cleansing is preferred to colonoscopy and shows moderate sensitivity (60-67%) for polyps of at least 10 mm in size without impaired diagnostic value at mSV levels as low as 0.7 mSv.

Florie, et al. "MR Colonography With Limited Bowel Preparation" (Radiology Volume 245: Number 1, October 2007) evaluated magnetic resonance (MR) colonography with limited bowel preparation compared with full-preparation colonoscopy in participants at increased risk for colorectal cancer. All participants were prepared with a low-fiber diet, lactulose, and an oral contrast agent 48 hours before MR imaging. All were sent a list summarizing what dietary measures were necessary (no fiber-rich food, no nuts). The lactulose (12 g Lactulose CF powder [6 g per sachet]; Centrafarm, Etten-Leur, the Netherlands) was dissolved in water and taken both days before MR colonography in the morning for stool softening. If the stool became too soft, participants were allowed to reduce the amount of lactulose (asked in questionnaire 2). Ten milliliters of a gadolinium chelate (gadopentetate dimeglumine 0.5 mmol/mL, Magnevist; Schering, Berlin, Germany) was added to all major meals during this period (six meals over 2 days) for stool tagging. Questions about stool consistency (diarrhea, soft stool, normal shaped), abdominal pain (yes, no), and flatulence (yes, no) were asked in questionnaire 2. Participants ingested 4 L of polyethylene glycol electrolyte solution (Klean-Prep; Helsinn Birex Pharmaceuticals, Dublin, Ireland) for bowel preparation the day before conventional colonoscopy (if the examination was performed in the morning) or 2 L on the day before and 2 L on the day of the examination (if the examination was performed in the afternoon). If necessary, additional solution was ingested. Participants were not allowed to eat after starting the bowel preparation. The colonoscopy was performed with a standard scope. The authors concluded that the study results showed that most (65%) participants at increased risk for colorectal cancer prefer MR colonography with limited bowel preparation to colonoscopy for their next examination when there is a 20% chance of having to undergo a therapeutic colonoscopy afterwards. In a questionnaire completed at home at least 5 weeks after the procedures, fewer participants preferred MR colonography, but most (65%) still preferred MR colonography with limited bowel preparation. This preference was mainly based on the limited bowel preparation necessary for MR colonography and the fact that less pain was experienced during MR colonography. Filling of the colon with water and the multiple breath holds necessary were considered the most burdensome factors of MR colonography.

Urita, et al. "Hydrogen Breath Test as an Indicator of the Quality of colonic Preparation for Colonoscopy" (Gastrointestinal Endoscopy Vol. 57, No. 2, 2003), reported the results of a study where patients undergoing colonoscopy were instructed (after fasting overnight) to ingest a polyethylene glycol solution containing 12 g lactulose at a rate of 50 ml every 5 minutes for 2 hours. The preparation for colonoscopy was judged to be poor in 18% and adequate in 82% of the patients.

U.S. Pat. Nos. 7,718,197 and 7,687,075 (Skiendzielewski, et al.) describe colonic purgative compositions in a solid tablet dosage form, comprising at least one purgative (e.g., sodium phosphate or lactulose) and at least one soluble, non-fermentable binder, such as polyethylene glycol. The compositions are designed to improve patient tolerance and compliance, while at the same time improving the quality of bowel cleansing prior to diagnostic and surgical procedures and are said to be useful in lower dosages as a laxative to promote elimination and/or to relieve constipation.

Due to their efficacy in constipation, prescription osmotic laxatives like Kristalose®, the dry powder form of lactulose marketed by Cumberland Pharmaceuticals Inc., have received some attention from gastroenterologists for use as a bowel evacuant prior to colonoscopy, but these effects have not been formally studied or documented. Patients reportedly regard this bowel preparation regimen as being more tolerable than traditional regimens. Kristalose is an FDA-approved drug for the treatment of chronic constipation and is a generic version of lactulose which has been in use for more than 30 years.

Currently, there are multiple purgatives approved for bowel evacuation prior to colonoscopy and these products are often described as foul tasting, harsh, and too voluminous. Therefore, a product and regimen that is more acceptable to patients would be beneficial. A more palatable and convenient process may increase patient compliance and satisfaction.

SUMMARY OF THE INVENTION

In accordance with the above objectives and others, the present invention is directed in part to a method of treating an adult patient in need of bowel evacuation by administering a bowel evacuant treatment consisting of consecutive doses of lactulose administered in a dosing regimen suitable to achieve bowel evacuation prior to a diagnostic, therapeutic or surgical procedure.

The present invention is further directed to a method of treating an adult patient in need of bowel evacuation by administering a bowel evacuant treatment consisting of a total of from about 180 g to about 220 g of lactulose administered in a dosing regimen suitable to achieve bowel evacuation prior to a diagnostic, therapeutic or surgical procedure. In certain preferred embodiments, the lactulose is administered in 1 dose, or the total dose is split into a plurality of doses from about 2 to about 22 doses, administered at suitable time intervals to effectuate bowel evacuation.

In certain preferred embodiments, the bowel evacuant treatment comprises or consists of a plurality of doses of lactulose administered at suitable time intervals to effectuate bowel evacuation for a total of about 2 to about 12 doses prior to a diagnostic, therapeutic or surgical procedure, such that the total dose of lactulose administered during the dosing regimen is from about 180 g to about 220 g. In certain embodiments, the dosing begins on the evening prior to the diagnostic, therapeutic or surgical procedure and the lactulose is administered in one dose or divided doses over a suitable time period to effectuate bowel evacuation in the patient. In certain preferred embodiments, the method further comprises administering the lactulose in dosages of about 10 to about 50 g each.

In preferred embodiments, the lactulose is administered in a suitable clear liquid such that a total of about 2 to about 2.5 liters of liquid are ingested along with the lactulose. In certain preferred embodiments, the clear liquid is water.

In certain preferred embodiments, the lactulose is administered at suitable time intervals until the total dose is of lactulose is administered. In certain preferred embodiments, the method includes administering the first dose of lactulose at about dinnertime on the evening prior to a diagnostic, therapeutic or surgical procedure, and thereafter administering additional doses of lactulose at suitable time intervals until the total dose is of lactulose is administered.

In certain preferred embodiments, the lactulose in the doses are administered about every 30 to about every 60 minutes, or to about every 120 minutes, until the total dose of lactulose is administered, depending, e.g., on the number of divided doses required for the patient to ingest the entire dose of about 180 g to about 220 g of lactulose. For example, in embodiments where the lactulose is administered in about 9 divided doses, the doses may be administered about every 30 minutes until the total dose of lactulose is administered. In embodiments where the lactulose is administered in about 4 doses, the doses may be administered about once every hour (for four hours) until the total dose of lactulose is administered. In certain embodiments, the lactulose may be administered in one dose. Alternatively, the dose of lactulose is divided into larger amounts (i.e., greater than 20 g to about 120 g), and the number of doses reduced, such that the total dose of lactulose administered being from about 180 g to about 220 g. Alternatively, each dose of lactulose may be a different amount, with the total dose of lactulose administered being from about 180 g to about 220 g. Alternatively, the lactulose dose may start off as a relatively large dose (e.g., about 40 g to about 120 g) and decrease in subsequent doses administered to the patient at suitable time intervals, with the total dose of lactulose being from about 180 g to about 220 g over the course of treatment. Alternatively, the lactulose dose may start off as a relatively small dose (e.g., 10 g or 20 g) and increase in subsequent doses administered to the patient at suitable time intervals, with the total dose of lactulose being from about 180 g to about 220 g over the course of treatment.

In preferred embodiments, the method further comprises instructing the patient to fast and only drink clear liquids during the administration of the lactulose doses and continuing until after the completion of the diagnostic or surgical procedure.

In certain preferred embodiments, the lactulose is supplied to the patient in the form of a powder. In certain further preferred embodiments, the lactulose is supplied to the patient in the form of one or more packets, each containing from about 10 to about 220 g of lactulose in powder form.

In certain preferred embodiments, the lactulose is combined with suitable additional ingredients, e.g., a suitable mount of a stool softener to aid in the evacuation of the colon of the patient(s). Alternatively, or in addition to the stool softener, in certain further preferred embodiments, the lactulose is combined with a suitable mixture of electrolytes to replenish the electrolytes excreted by the patient(s) as a result of the dosing regimen. Such additional ingredients are not bowel evacuants, but rather aide in the method of treatment.

In embodiments of the invention in which the lactulose is supplied in powder form, the methods further comprise instructing the patient to dissolve the lactulose in a suitable amount of liquid prior to ingesting the same. The amount of liquid can be varied, depending on the amount of lactulose to be administered as a single dose. In one such embodiment, the lactulose is supplied as 20 g of lactulose powder and is dissolved in about 4 ounces (about 120 ml) of water. This is preferably accomplished by instructing the patient to dissolve the lactulose powder in water by pouring the lactulose powder into the water while stirring until the crystals are dissolved, such that the resulting solution is a clear, colorless to a slightly pale yellow color.

The bowel evacuation procedure may be performed prior to any diagnostic or surgical procedure requiring bowel, gastrointestinal or colon evacuation. Such procedures include but are not limited to colonoscopy, sigmoidoscopy, barium enema examination, colon surgery, gastrointestinal testing, fiberoptic screening, pilloscopy viral colonoscopy, gastrointestinal surgery, colostomy, ileostomy, computed tomography colonography (CTC), and magnetic resonance (MR) colonography. In certain preferred embodiments, the methods of the invention are used for the treatment of adult human patients prior to carrying out a colonoscopy, a fiberoptic screening colonoscopy, a virtual colonoscopy, a sigmoidoscopy, a computed tomography colonography (CTC), a magnetic resonance (MR) colonography, or a flexible sigmoidoscopy.

In additional embodiments, the invention is directed to a method of preparing an adult human for a diagnostic, therapeutic or surgical procedure requiring bowel evacuation, comprising ingesting a bowel evacuant treatment comprising or consisting of separate or consecutive doses of 20 g lactulose administered every 30 minutes for a total of 9 doses beginning on the evening prior to the diagnostic or surgical procedure. This dosing regimen is particularly suited for situations in which the diagnostic, therapeutic or surgical procedure requiring bowel evacuation is scheduled to take place the following morning, but can also be suitable to procedures the following afternoon.

In other embodiments, the invention is directed to a method of preparing an adult human for a diagnostic, therapeutic or surgical procedure requiring bowel evacuation, comprising ingesting a bowel evacuant treatment comprising or consisting of separate or consecutive doses of lactulose at suitable time intervals beginning in the evening prior to the diagnostic, therapeutic or surgical procedure, and thereafter ingesting the remaining dose(s) of lactulose at suitable intervals the next morning, such that the total dose of lactulose administered during the dosing regimen (course of treatment) is from about 180 g to about 220 g. This dosing regimen is particularly suited for situations in which the diagnostic, therapeutic or surgical procedure requiring bowel evacuation is scheduled to take place in the afternoon, rather than in the morning. For example, in this embodiment, 20 g lactulose may be administered every 30 minutes for a total of 4-6 doses beginning on the evening prior to the diagnostic, therapeutic or surgical procedure, and thereafter 2-8 additional doses of 20 g lactulose may be administered every 30 minutes the next morning (the morning of the diagnostic, therapeutic or surgical procedure), such that the total dose of lactulose administered is from about 180 g to about 220 g. Alternatively, the dose of lactulose is divided into larger amounts (i.e., greater than 20 g), and the number of doses reduced, such that the total dose of lactulose administered being from about 180 g to about 220 g. Further, the lactulose doses may be divided into differing doses over the course of treatment, with the total dose of lactulose administered being from about 180 g to about 220 g. For example, the lactulose may be administered as larger doses (e.g., from about 30 g to about 80 g lactulose) per dose in the evening prior to the procedure and administered in smaller doses (e.g., from about 10 g to about 40 g lactulose per dose) on the morning of the procedure, with the total dose of lactulose administered being from about 180 g to about 220 g. Alternatively, the lactulose dose may start off as a relatively large dose (e.g., about 40 g to about 120 g) and decrease in subsequent doses administered to the patient at suitable time intervals, with the total dose of lactulose being from about 180 g to about 220 g over the course of treatment. Alternatively, the lactulose dose may start off as a relatively small dose (e.g., 10 g or 20 g) and increase in subsequent doses administered to the patient at suitable time intervals, with the total dose of lactulose being from about 180 g to about 220 g over the course of treatment.

As a general rule, the lactulose may be dissolved in a proportion of 4 ounces or 120 ml of clear liquid (e.g., water) per 20 g lactulose. However, a person having ordinary skill in the art will appreciate that this proportion is variable on many factors, including temperature and the particular clear liquid used. All such obvious variations of the present invention, and other variations that would be obvious to those persons having ordinary skill in the art, are contemplated to be within the scope of the appended claims.

In certain preferred embodiments, the patient is instructed to drink from about 2 to about 2.5 liters of fluid (e.g., water, apple juice or a sports drink (e.g. Gatorade®)) on the day before the colonoscopy (about 60 to about 80 ounces, or about 1775 ml to about 2366 ml).

In certain embodiments, the dosing regimen of lactulose is about nine 20 g doses (dissolved in fluid as per above, one dose every 30 minutes for 4 hours) taken the evening before the colonoscopy procedure. In certain preferred embodiments, if the patient has a history of constipation or is chronically being administered a lot of laxatives, the patient may then be administered two additional doses of 20 g (each dose) of lactulose, for a total of eleven 20 g lactulose doses, instead of 9 doses. Alternatively, the dosing regimen may comprise one additional dose of 40 g. In embodiments in which the lactulose is supplied in powder form, the patient may therefore be administered that 40 g dose contained in one or more packets. For example, the 40 g dose may be contained in two additional containers (e.g., packets) of lactulose, each containing 20 g lactulose.

In certain embodiments of the invention, the patient is instructed to take a suitable dose of lactulose every 30 minutes such that from about 8 to about 15 doses of lactulose are administered over the course of therapy, containing a total of from about 180 to about 220 g lactulose, in accordance with the above-described methods of the present invention.

In further embodiments of the invention, the dosing regimen consists of one packet of lactulose that contains the entire dosage of lactulose for the dosing regimen (e.g., about 180-220 g lactulose), which can be dissolved in a pitcher. The patient then ingests the mixture in suitable divided dosages over the requisite period of time (e.g., from about 3 to about 6 hours on the night prior to the diagnostic, therapeutic or surgical procedure requiring bowel evacuation).

In other embodiments of the invention, the dosing regimen consists of four packets of lactulose that together contain a total of from about 180 to about 220 g lactulose (such that each packet contains from about 45 g to about 55 g lactulose. The patient could then ingest the mixture in divided doses over a suitable time period, e.g., four doses taken once an hour for four hours.

In certain other embodiments of the invention, the dosing regimen consists packets of lactulose that together contain a total of from about 180 to about 220 g lactulose, such that each packet contains from about 45 g to about 110 g lactulose.

In certain preferred embodiments, the method further comprises instructing the patient to drink at least about 64 ounces of water, apple juice or a sports drink (e.g. Gatorade®) throughout the day before the diagnostic, therapeutic or surgical procedure (e.g., colonoscopy). Therefore, in such preferred embodiments, the patient ingests, in addition to the 36 ounces of water that are used to mix the Kristalose, for a total fluid amount of 100 ounces.

In certain preferred embodiments, the method further comprises instructing the patient to begin ingesting the first dose of lactulose at about 5 pm the evening prior to the day on which the diagnostic, therapeutic or surgical procedure (e.g., colonoscopy) is to be performed, if at all possible.

In certain preferred embodiments, the patient is instructed to ingest a low-fiber diet prior to the diagnostic, therapeutic or surgical procedure (e.g., colonoscopy), preferably from about 3 to about 4 days prior to the day on which the diagnostic, therapeutic or surgical procedure (e.g., colonoscopy) is to be performed.

Further embodiments of the invention are directed to a kit for use in a regimen for bowel evacuation, the kit including a bowel evacuant treatment consisting of from about 1 to about 22 containers of lactulose, containing a total of from about 180 g to about 220 g lactulose (e.g., in correspondingly divided doses to the number of containers). For example, the bowel evacuant treatment may comprise or consist of about 9 containers (e.g., packets), each container containing 20 grams of lactulose in powder form. In certain preferred embodiments, the container is a pouch or a packet. In certain embodiments, the kit may further comprise a measuring and/or mixing device. In yet further embodiments, the kit includes a patient record for recording the time and/or number of doses and/or amount of the dose ingested. The patient record may be a device which allows the patient, or a third person (e.g., physician, nurse practioner or nurse, friend or family member) to electronically or by hand writing record the ingestion of doses (dose number and/or dosage and/or time of administration). An electronic device may further include a wired or wireless mechanism or means for transferring the recorded data to someone overseeing the therapy, e.g., a physician or nurse. In certain preferred embodiments, the kit further comprises instructions for dissolving the powder. In certain preferred embodiments, the kit further comprising instructions for the patient to self-administer the lactulose by dissolving lactulose contained in each pouch as a dose in a suitable amount of water (e.g., about 4 ounces per 20 g lactulose) by pouring the lactulose powder into water while stirring continuously until the crystals are dissolved and the resultant solution is a colorless to a slightly pale yellow, and ingesting the dose every 30 minutes for a total of 9 doses beginning on the evening prior to a diagnostic or surgical procedure.

In certain embodiments, the kit includes from about 1 to about 6 additional containers (e.g., packets) of lactulose, preferably about 2 additional containers (e.g., packets), each containing holding 20 g lactulose. In such embodiments, the patient is instructed whether or not to ingest the additional packets (doses) of lactulose. In certain preferred embodiments, the patient is instructed to ingest the additional doses of lactulose if the patient has a history of constipation or is chronically being administered a lot of laxatives. In certain preferred embodiments, the kit therefore would include, e.g., about 11 packets of lactulose.

A method of the present invention may be used to cleanse the colon prior to carrying out a diagnostic, therapeutic or surgical procedure on the colon, rectum or anus or elsewhere in the abdomen. A diagnostic or surgical procedure may, for example, be colonoscopy, barium enema examination, sigmoidoscopy or colon surgery. The method of the present invention may also be used in the treatment of acute gastrointestinal infections, for example bacterial or viral gastroenteritis.

As used herein the term "treat," "treating" or "treatment" refers to the administration of lactulose to an adult individual who is in need of bowel evacuation.

As used herein the term "container" encompasses enclosures for the lactulose with or without optional additional (nonlaxative) ingredients, preferably made out of a moisture resistant material. In certain preferred embodiments, the container comprises foil packets. It also encompasses bags, films, tubes, bottles, and boxes, preferably made out of a moisture resistant material.

As used herein, the term "bowel evacuant" or "bowel evacuant treatment" refers to an active agent that causes bowel evacuation, and does not encompass other agents which may aid in the process such as electrolytes and stool softeners. The phrase "bowel evacuant treatment consisting of . . . lactulose" is meant to exclude the administration/inclusion of other bowel evacuant agents, such as polyethylene glycol.

DETAILED DESCRIPTION OF THE INVENTION

Lactulose is a colonic acidifier which promotes laxation. The chemical name for lactulose is 4-O-b-D-Galactopyranosyl-D-fructofuranose. The molecular formula is $C_{12}H_{22}O_{11}$. The molecular weight is 342.30. It is freely soluble in water.

Lactulose is a disaccharide: a sugar molecule composed of two smaller sugar molecules, fructose and galactose, bonded together. Lactulose is poorly absorbed from the gastrointestinal tract and no enzyme capable of hydrolysis of this disaccharide is present in human gastrointestinal tissue. As a result, oral doses of lactulose reach the colon virtually unchanged. In the colon, lactulose is broken down primarily to lactic acid, and also to small amounts of formic and acetic acids, as well as carbon dioxide gas, by the action of colonic bacteria, which results in an increase in osmotic pressure and slight acidification of the colonic contents. This in turn causes an increase in stool water content and softens the stool, hence the common use of lactulose as a laxative. Lactulose has been in use as a laxative for more than 30 years. In patients with a history of chronic constipation, lactulose therapy increases the number of bowel movements per day and the number of days on which bowel movements occur.

The lactulose product used in the present invention may be any product that is commercially available. It may be in a syrup or liquid form, or may be dispensed to the patient in the form of a dry powder which is reconstituted by the patient prior to ingestion at the beginning of the bowel preparation for colonoscopy.

In a preferred embodiment, the lactulose product is Kristalose®, a dry powder form of lactulose (syrup/liquid formulation) which is commercially marketed by Cumberland Pharmaceuticals, Inc. Kristalose is an FDA-approved drug for the treatment of chronic constipation.

Kristalose is a synthetic disaccharide in the form of crystals for reconstitution prior to use for oral administration. Each 10 g of lactulose contains less than 0.3 g galactose and lactose as a total sum. The pH range is 3.0 to 7.0. Kristalose (Lactulose) for oral solution is available in single dose packets of 10 g (NDC 66220-719-01) and single dose packets of 20 g (NDC 66220-729-01). The packets are currently supplied as follows: NDC 66220-719-30 (Carton of thirty 10 g packets) and NDC 66220-729-30 (Carton of thirty 20 g packets). Kristalose is prepared for administration by dissolving the contents of a packet in half a glass (4 ounces) of water. When Lactulose For Oral Solution is dissolved in water, the resulting solution may be colorless to a slightly pale yellow color.

A study in patients with chronic constipation has been completed for Kristalose to evaluate patient preference between powder (Kristalose) and liquid lactulose in terms of overall preference, taste, consistency, and portability; and safety in terms of adverse events. Three sites randomized patients (total N=50) to powder or liquid lactulose for 7 days with crossover. Patient preference was assessed by a questionnaire, and the occurrence of adverse events was monitored. Of those expressing a preference, 44% and 57% more patients preferred the taste and consistency, respectively, of powder over liquid lactulose. More than six-times as many patients preferred the portability of powder compared to liquid lactulose, and overall, 77% more patients preferred powder over liquid lactulose. There was no difference between treatment groups in terms of adverse events (p=0.635). A manuscript describing this study is in press at Clinical and Experimental Gastroenterology and the study is registered on clinicaltrials.gov (NCT00712543).

In certain preferred embodiments, the bowel evacuation performed in accordance with the present invention is accomplished prior to carrying out a diagnostic, therapeutic or surgical procedure on the colon, rectum or anus or elsewhere in the abdomen. The diagnostic or surgical procedure may, for example, be colonoscopy, barium enema examination, sigmoidoscopy or colon surgery, gastrointestinal testing, fiberoptic screening, pilloscopy viral colonoscopy, gastrointestinal surgery, colostomy or ileostomy. In certain preferred embodiments, the bowel evacuation is performed prior to carrying out colonoscopy, fiberoptic screening colonoscopy, virtual colonoscopy, sigmoidoscopy, computed tomography colonography (CTC), magnetic resonance (MR) colonography, or flexible sigmoidoscopy.

In accordance with the methods of the present invention, the adult patient(s) in need of bowel evacuation is administered (or self-administers) a dosing regimen designed to provide the patient with a total dose of from about 180 g to about 220 g lactulose, dissolved in a suitable amount of water, in a plurality of doses, and preferably from about 4 to about 12 total doses. The dosing regimen further includes the ingestion of a total of from about 2 to about 2.5 liters of clear liquid. The lactulose is preferably dissolved in all or part of this total amount of fluid. Thus, in certain preferred embodiments, the dosing regimen may comprise a total of 9 separate doses of lactulose, each dose comprising 20 g lactulose dissolved in about four ounces (120 ml) of clear liquid (e.g., water).

Alternatively, the dosing regimen may comprise 40 g or lactulose in about 8 ounces of clear liquid administered 5 times over 4 hours.

In other embodiments, the dosing regimen may comprise a total of 8 separate doses of lactulose, each dose comprising 22.5 g lactulose dissolved in about five ounces (150 ml) of clear liquid.

The doses are preferably administered, e.g., at 30 minute time intervals beginning at around 5-6 pm the evening before the procedure requiring bowel evacuation.

A person having ordinary skill in the art would appreciate that one could modify these dosing regimens and still obtain the required total dose of lactulose and liquid administered over a suitable amount of time to effectuate suitable bowel evacuation of the patient(s).

One such dosing regimen could consist of one packet of lactulose that contains the entire dosage of lactulose for the dosing regimen (e.g., about 180-220 g lactulose), which can be dissolved in a pitcher with a suitable amount of clear liquid (e.g., about 36-44 ounces or about 1-1.32 liters). The patient could then ingest the mixture in divided doses over a suitable time period (e.g., four doses taken once an hour for four hours, or eight doses taken once every 30 minutes for four hours, and the like).

Another such dosing regimen could consist of four packets of lactulose that, in total, from about 180 to about 220 g lactulose (such that each packet contains from about 45 g to about 55 g lactulose. The patient could then ingest the mixture in divided doses over a suitable time period, e.g., four doses taken once an hour for four hours.

In certain additional preferred embodiments, the dosing regimen may be modified for situations where the procedure requiring bowel evacuation is not scheduled until the next afternoon following the beginning of treatment with lactulose. In such embodiments, the bowel evacuant treatment may comprise or consist of separate or consecutive doses of lactulose administered at suitable time intervals (e.g., every 30 minutes) for a total of 2-4 doses beginning on the evening prior to the diagnostic or surgical procedure, and thereafter at least 1 dose or at least 2 additional doses of lactulose administered at suitable time intervals (e.g., every 30 minutes) the next morning. A person having ordinary skill in the art would appreciate that one could modify these dosing regimens and still obtain the required total dose of lactulose and liquid administered over a suitable amount of time to effectuate suitable bowel evacuation of the patient(s).

All permutations of the dosing regimens outlined above are considered to be equivalents of the present methods set forth herein and claimed, and are considered to be encompassed by the appended claims.

Further, it should be understood that in the above embodiments and others, the total amount of lactulose and the total number of administered doses may be modified to suit the particular situation and the needs of the patient. Thus, it is contemplated that the dosing regimens of the present invention may comprise from about 1 to about 22 containers (e.g., packets) of lactulose containing in total from about 180 g to about 220 g lactulose, in accordance with the above-described methods of the present invention.

Regardless of the dosing regimen, the invention herein described contemplates the co-administration of a total of from about 2 to about 2.5 liters of clear liquid. Clear liquids are defined for purposes of the present invention as liquids that are easy to see through and to pour.

Clear liquids include, but are not limited to, water, clear fruit juices (such as apple or cranberry juices), clear sodas (e.g., ginger ale or lemon-lime soda, but not cola), an electrolyte replacement and/or sport drink (e.g. Gatorade®), tea or coffee (without milk, cream, flavored cream, or creamer substitutes), clear soup broths (e.g., a bouillon cube dissolved in water, without any additional ingredients), and the like.

A clear liquid diet is not nutritionally adequate and should only be followed for a short period of time. The patient can ingest gelatin with no fruit or other ingredients, or ice pops, with no fruit pulp or fruit bits in them, or hard candy to provide some nutrition during the dosing regimen.

Due to the loss of electrolytes that are passed from the body in the stool of the patient, in certain preferred embodiments the dosing regimen also includes a dose(s) of electrolytes to replace the electrolytes passed from the body in the stool. In certain preferred embodiments, the electrolytes included in the dosing regimen include one or both of the following salts: sodium chloride in an amount from about 5 g to about 12 g, and preferably from about 5.4 g to about 11.5 g; potassium chloride in an amount from about 0.5 g to about 4 g, and preferably from about 0.7 to about 3 g. In certain preferred embodiments, the dosing regimen further includes the following buffers/acids: sodium bicarbonate in an amount from about 0 to about 7 g, and preferably from about 2.8 to about 6.75 g; sodium sulfate in an amount from about 0 to about 23 g, preferably from about 15 g to about 22.75 g; ascorbic acid in an amount from about 0 to about 12 g; and sodium ascorbate in an amount from about 0 to about 12 g. It should be emphasized that these amounts are total amounts of the ingredient over the entire dosing regimen. It is further contemplated that these ingredients can be appropriately divided and admixed in, e.g., equally divided doses together with the lactulose powder and placed in a container (e.g., packet) for reconstitution with clear liquid by the patient. Alternatively, the electrolyte can be separately contained in containers (e.g., packets) to be dissolved along with a packet of lactulose. In yet other embodiments, the electrolytes may simply be separately (from the lactulose) added to the total volume of clear fluid and administered to the patient.

In certain preferred embodiments, the dosing regimen further includes the administration of a stool softener such as colace (also known as dioctyl sodium sulfosuccinate or docusate sodium). In certain preferred embodiments, the total amount of colace administered over the dosing regimen is from about 50 mg to about 360 mg. It is further contemplated that the colace can be appropriately divided and admixed in, e.g., equally divided doses together with the lactulose powder and placed in a container (e.g., packet) for reconstitution with clear liquid by the patient. Alternatively, the colace can be separately contained in containers (e.g., packets) to be administered along with a packet of lactulose. In yet other embodiments, the electrolytes or the stool softener (e.g., colace) may simply be separately administered to the patient during the dosing regimen.

Further embodiments of the invention are directed to a kit for use in a regimen for bowel evacuation. The kit includes a bowel evacuant treatment consisting of, e.g., a suitable number of containers (e.g., packets) containing lactulose, such that the total amount of lactulose contained in the packets is from about 180 g to about 220 g. In certain preferred embodiments, the kit includes a bowel evacuant treatment consisting of from 1 to about 22 containers (e.g., packets), each container containing a suitable dose of lactulose in powder form, such that the total amount of lactulose contained within the containers in the kit is from about 180 g to about 220 g. In certain preferred embodiments, the kit includes a bowel evacuant treatment consisting of from about 8 to about 12 containers (e.g., packets; preferably 9 packets), each container containing a suitable dose of lactulose in powder form (e.g., 20 g). In certain additional preferred embodiments, the kit may further include from about 1 to about 6 additional containers (e.g., packets) of lactulose, preferably about 2 additional containers (e.g., packets), each containing holding another suitable dose of lactulose (e.g., 20 g). Further embodiments of the invention are directed to a kit for use in a regimen for bowel evacuation. The kit includes a bowel evacuant treatment consisting of, e.g., a suitable number of containers (e.g., packets) containing lactulose, such that the total amount of lactulose contained in the packets is from about 180 g to about 220 g.

In certain preferred embodiments, the kit further includes a dose of one or more of the above-mentioned electrolytes and buffers/acids. In such embodiments, the dose of one or more of the above-mentioned electrolytes and/or buffers/acids may be contained as divided doses together with the doses of lactulose. On the other hand, the kit may include separate containers (e.g., packets) containing divided doses or one total dose of the above-mentioned electrolytes and/or buffers/acids, along with instructions for administration.

The following example represents specific embodiments of the present invention, and is not representative of the entire scope of the invention.

Detailed Description of Preferred Embodiments

EXAMPLE 1

In Example 1, 20 patients were enrolled in a single center, open-label, pilot study in adult patients requiring bowel evacuation for colonoscopy Safety, efficacy, and patient tolerability/preference of Kristalose as a bowel evacuant, and pre- and post-dose hydrogen and methane gas production were assessed.

The primary objective of the study was to determine whether Kristalose causes a potentially dangerous increase in hydrogen and/or methane gas levels in patients requiring bowel evacuation. Therefore, to evaluate the primary objective of hydrogen and methane gas production, pre- and post-dose breath analysis for hydrogen and methane gas was measured.

The secondary objectives of this study were to determine the efficacy of Kristalose as a bowel evacuant, as assessed by the physician's determination of the cleanliness of the colon; to determine the incidence of treatment failure (Boston bowel prep score <5, and/or any colon segment score of 0); to evaluate the patient tolerability of and preference for Kristalose as a bowel evacuant as assessed by a patient questionnaire (Table 1); and to evaluate the safety of Kristalose as a bowel evacuant, as determined by the incidence and severity of treatment emergent adverse events. Table 1 is set forth below:

To evaluate the secondary objective of efficacy, the following endpoints were be measured: Physician's determination of the cleanliness of the colon will be evaluated by completion of the Boston bowel prep scale; and the number and percentage of patients who by the physician's determination are considered treatment failures (patients with insufficient evacuation of the bowel=Boston bowel prep score <5, and/or any colon segment score of 0, as determined by the Boston bowel prep scale).

Other secondary objectives of the study of Example 1 included evaluating the safety of Kristalose as a bowel evacuant, as determined by the incidence and severity of treatment emergent adverse events; and evaluating the secondary objective of efficacy.

The physician's determination of the cleanliness of the colon was be evaluated by completion of the Boston bowel prep scale. The Boston Bowel Preparation Scale was developed for evaluating the quality of bowel preparation during colonoscopy. The preparation scales uses a number from 0 to 3 to rate each of three sections of the colon; the right colon, the transverse colon, and the left colon. Decimal point scores should not be used. The individual segment scores are then summed for a total score ranging from 0 to 9. The hepatic flexure and the splenic flexure will be considered parts of the transverse colon using the scale. These scores were assigned to the colon segment based upon the appearance after any maneuvers; such as washing, suctioning, or movement of debris and are meant to be applied during the withdrawal phase of colonoscopy.

The secondary objective of efficacy was evaluated by the physician's determination of the cleanliness of the colon. This was accomplished Using the Boston Bowel Preparation Scale, a segment score of 0 (zero) describes an unprepared colon segment with mucosa not seen due to solid stool or thick liquid stool that cannot be cleared. A segment score of 1 describes a segment where a portion of mucosa of the colon segment seen, but other areas of the colon segment not well seen due to staining, residual stool and/or opaque liquid. A segment score of 2 describes a segment where in there is a minor amount of residual staining, small fragments of stool and/or opaque liquid, but mucosa of colon segment seen well. Finally, a segment score of 3 describes a segment wherein the entire mucosa of colon segment seen well with no residual staining, small fragments of stool or opaque liquid. Each segment of the colon (Right, Transverse (the Transverse Colon, and Left is should be rated based on the cleanliness of the colon from 0 to 3; then the entire score is added.

The secondary objective of efficacy was also evaluated by the number and percentage of patients who by the physician's determination are considered treatment failures (patients with insufficient evacuation of the bowel=Boston bowel prep score <5, and/or any colon segment score of 0).

Safety was evaluated on the basis of the treatment of emergent adverse events.

Each patient received a total of 9 pouches of 20 grams of Kristalose. Each pouch of Kristalose is dissolved into 4 ounces of water by pouring the Kristalose powder into the water while stirring continuously until the crystals are dissolved. When Kristalose for oral solution is dissolved in water, the resulting solution is a colorless to a slightly pale yellow color.

Participants will take took a total of nine 20-gram doses of Kristalose, one dose every thirty (30) minutes for four consecutive hours the evening before the colonoscopy procedure (before the patient went to bed—Table 2). Dosing the night before the procedure was consistent with other bowel preps. The physician will also instructed the patient to fast and only drink clear liquids during this dosing period and up until the completion of the colonoscopy procedure (see Patient instructions—Table 2). In order to be eligible for participation in the analysis, patients must completed the prescribed regimen (as recorded in the patient diary).

TABLE 2

Dosing Schedule

| Study Time (hrs) | 0 | 0.5 | 1 | 1.5 | 2 | 2.5 | 3 | 3.5 | 4 |
|---|---|---|---|---|---|---|---|---|---|
| Dose # | 1 | 2 | 3 | 4 | 5 | 6 | 7 | 8 | 9 |

The package insert for Kristalose states that enteric bacteria may convert a portion of the dose into hydrogen and methane gases. Production of these gases may cause a risk to the patient during cautery endoscopy procedures, as the cautery may ignite these gases at levels above their established explosive threshold during the procedure causing a fire or explosion. Therefore, each subject underwent a breath analysis assessment within 15 to 180 minutes prior to the colonoscopy procedure to determine whether lactulose causes an unsafe buildup of these hydrogen and methane gases. The hydrogen risk threshold is 40,000 ppm and the methane threshold is 50,000 ppm, the established levels above which combustion may occur. Patients with gas levels above these thresholds may still undergo colonoscopy but were not to be offered polypectomy with cautery because of the risk of explosion; thus some patients (perhaps 5%) may need to repeat their colonoscopy at some point in the near future if a large polyp is found and cannot be removed. The primary endpoint (hydrogen and methane gas production) was assessed in all patients who completed the study drug dosing regimen and safety was assessed in all patients who took at least one dose of study drug.

The demographics of the subjects who participated in the study are set forth in Table 3 below:

TABLE 3

Demographics

| | | |
|---|---|---|
| N | | 20 |
| Gender | | 15 female/5 male* |
| Age (yrs.) | Mean (SD) | 57.5 (11.6) |
| | Range | (30.3-83.6) |
| Height (in.) | Mean (SD) | 67 (3.8) |
| | Range | (61-75) |
| Weight (lbs.) | Mean (SD) | 164 (47) |
| | Range | (117-293) |

*All patients were white and non-hispanic

The results of the study are set forth in Table 4 below:

TABLE 4

| Breath Analyses | | |
|---|---|---|
| Breath Hydrogen Level Pre-Prep (Baseline) | Mean (SD) range | 13 (17) (2-74) |
| Breath Hydrogen Level Post-Prep | Mean (SD) range | 44 (44) (1-175) |
| Breath Methane Level Pre-Prep (Baseline) | Mean (SD) range | −2 (4) (−5-16) |
| Breath Methane Level Post-Prep | Mean (SD) range | −3 (0.6) (−6 to −2) |
| Bowel Cleanliness | | |
| Boston Bowel Prep Score | Mean (SD) Median Range | 7.5 (1.36) 8.0 (4.0-9.0) |
| Treatment Failure (Boston Bowel Prep Score <5 or any segment score of 0) Incidence (%) | | 1/20# (5%) |
| Preference/Questionnaire | | |
| No. of Patients with Previous Bowel Prep | | 15 8* GoLytely, 2* Fleets Phospho Soda, 1 Visical, 5 Unknown |
| No.(%) of Patients with Previous Bowel Prep that Preferred Crystalline Lactulose Bowel Prep | | 15 (100%) |

Patient did not take 64 oz. of additional fluid as instructed
*One patient had two previous bowel preps Conclusion It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

We claim:

1. A method of treating an adult patient in need of bowel evacuation by administering at least one dose of a bowel evacuant treatment consisting of a total of from about 180 g to about 220 g of lactulose in a dosing regimen suitable to achieve bowel evacuation prior to a diagnostic, therapeutic or surgical procedure, such that adequate visualization of the bowel is provided and a Boston bowel preparation scale score of 5 or more is achieved.

2. The method of claim 1, further comprising administering the bowel evacuant treatment in a plurality of doses of lactulose at suitable time intervals for a total of about 2 to about 22 doses prior to a diagnostic, therapeutic or surgical procedure, such that the total dose of lactulose administered during the dosing regimen is from about 180 g to about 220 g.

3. The method of claim 1, further comprising administering the bowel evacuant treatment in a plurality of doses of lactulose administered at suitable time intervals to effectuate bowel evacuation for a total of about 2 to about 12 doses prior to a diagnostic, therapeutic or surgical procedure.

4. The method of claim 3, wherein the doses are administered about every 30 to 60 minutes until the total dose of lactulose is administered.

5. The method of claim 4, further comprising administering the lactulose dissolved in a suitable clear liquid, and administering a total of about 2 to about 2.5 liters of clear liquid in addition to the amount of fluid contained in the doses of lactulose administered to the patient.

6. The method of claim 2, further comprising administering the first dose of lactulose at about dinnertime on the evening prior to a diagnostic, therapeutic or surgical procedure, and thereafter administering additional doses of lactulose at suitable time intervals until the total dose is of lactulose is administered.

7. The method of claim 6, further comprising administering the lactulose in dosages of about 10 to about 110 g each.

8. The method of claim 6, further comprising dissolving each dose of lactulose in a suitable amount of clear liquid prior to administering the lactulose dose to the patient.

9. The method of claim 7, further comprising dissolving the dose of lactulose in a proportion of about 20 g lactulose per 120 ml clear liquid.

10. The method of claim 1, wherein the diagnostic, therapeutic or surgical procedure is to be conducted in the afternoon, further comprising administering a plurality of doses of lactulose at suitable time intervals in the late evening on the day prior to the diagnostic, therapeutic or surgical procedure, and thereafter ingesting the remaining doses of lactulose at suitable time intervals the next morning.

11. The method of claim 1, further comprising instructing the patient to fast and only drink clear liquids during the administration of the lactulose doses and continuing until after the completion of the diagnostic or surgical procedure.

12. The method of claim 6, wherein the bowel evacuant treatment is being performed prior to a procedure selected from the group consisting colonoscopy, sigmoidoscopy, barium enema examination, colon surgery, gastrointestinal testing, fiberoptic screening, pilloscopy viral colonoscopy, gastrointestinal surgery, colostomy, ileostomy, computed tomography colonography (CTC), and magnetic resonance (MR) colonography.

13. The method of claim 10, wherein the bowel evacuant treatment is performed prior to carrying out a colonoscopy, a fiberoptic screening colonoscopy, a virtual colonoscopy, a sigmoidoscopy, a computed tomography colonography (CTC), a magnetic resonance (MR) colonography, or a flexible sigmoidoscopy.

14. The method of claim 8, wherein the procedure is a colonoscopy, further comprising performing the colonoscopy without polypectomy with cautery.

15. The method of claim 1, further comprising instructing the patient to drink from about 2 to about 2.5 liters of fluid on the day before the colonoscopy, in addition to the amount of fluid contained in the doses of lactulose administered to the patient.

16. The method of claim 1, wherein the patient has a history of constipation or is chronically being administered a lot of laxatives, further comprising instructing the patient to ingest at least two additional doses of 20 g (each dose) of lactulose.

17. The method of claim 1, further comprising instructing the patient to begin ingesting the first dose of lactulose promptly at about 5 pm the evening prior to the day on which the diagnostic, therapeutic or surgical procedure is to be performed.

18. The method of claim 12, further comprising instructing the patient to ingest a low-fiber diet prior to the diagnostic, therapeutic or surgical procedure from about 3 to about 4 days prior to the day on which the diagnostic, therapeutic or surgical procedure is to be performed.

19. The method of claim 5, further comprising administering a stool softener to the patient during the bowel evacuant treatment.

20. The method of claim 5, further comprising administering an additional agent selected from the group consisting of electrolytes, buffers/acids, and mixtures thereof during the bowel evacuant treatment.

21. The method of claim 5, further comprising administering effective amounts of an additional agent during the treatment selected from the group consisting of sodium chloride, potassium chloride, sodium bicarbonate, sodium sulfate, ascorbic acid, sodium ascorbate, and mixtures of any of the foregoing.

22. The method of claim 5, further comprising administering additional agents during the treatment selected from the group consisting of sodium chloride in an amount from about 5 g to about 12 g; potassium chloride in an amount from about 0.5 g to about 4 g; sodium bicarbonate in an amount from about 0 to about 7 g; sodium sulfate in an amount from about 0 to about 23 g; ascorbic acid in an amount from about 0 to about 12 g; sodium ascorbate in an amount from about 0 to about 12 g, and mixtures of any of the foregoing.

23. The method of claim 22, further comprising admixing suitable amounts of the additional agents with the lactulose and packaging the mixture in separate containers.

24. A method of preparing an adult human for a diagnostic, therapeutic or surgical procedure requiring bowel evacuation, comprising administering to a human patient a bowel evacuant treatment consisting of a plurality of lactulose doses in an amount of about 20 g dissolved in a clear liquid administered every 30 minutes for a total of 9 to about 11 doses beginning on the evening prior to the diagnostic or surgical procedure, such that a total of about 180 g to about 220 g lactulose is administered, such that adequate visualization of the bowel is provided and a Boston bowel preparation scale score of 5 or more is achieved.

25. A kit for use in a regimen for bowel evacuation of a human patient prior to a diagnostic, therapeutic or surgical procedure, said kit including a bowel evacuant treatment consisting of a single dose or divided doses of a bowel evacuant consisting of lactulose, together with optional additional ingredients selected from electrolytes, buffers/acids, a stool softener, and mixtures of any of the foregoing, the kit containing total amount of lactulose from about 180 g to about 220 g, the kit designed to provide adequate visualization of the bowel and a Boston bowel preparation scale score of 5 or more when administered to a human patient.

26. The kit of claim 25, wherein the kit comprises from about 9 to about 11 containers, each container containing a dose of about 20 grams of lactulose in powder form.

27. The kit of claim 26, wherein each container comprises a pouch or packet, further comprising instructions for the patient to self-administer the lactulose by dissolving lactulose contained in each pouch or packet as a dose in about 4 ounces of water by pouring the lactulose powder into water while stifling continuously until the crystals are dissolved and the resultant solution is a clear, colorless to a slightly pale yellow, and ingesting the dose every 30 minutes for a total of at least 9 doses beginning on the evening prior to a diagnostic or surgical procedure.

28. The kit of claim 26, wherein each container comprises a pouch or packet, and wherein the kit includes from about 1 to about 6 additional pouches or packets of lactulose, and instructions for the patient to ingest additional doses of lactulose if the patient has a history of constipation or is chronically being administered a lot of laxatives.

29. The kit of claim 25, further comprising an effective dose of a stool softener to be administered to the patient during the bowel evacuant treatment.

30. The kit of claim 25, further comprising an effective dose of electrolytes and buffers/acids to be administered to the patient during the bowel evacuant treatment.

31. The kit of claim 30, wherein said electrolytes and buffers/acids comprise effective amounts of an additional agent selected from the group consisting of sodium chloride, potassium chloride, sodium bicarbonate, sodium sulfate, ascorbic acid, sodium ascorbate, and mixtures of any of the foregoing.

32. The kit of claim 30, further comprising a dose of electrolytes and buffers/acids selected from the group consisting of sodium chloride in an amount from about 5 g to about 12 g; potassium chloride in an amount from about 0.5 g to about 4 g; sodium bicarbonate in an amount from about 0 to about 7 g; sodium sulfate in an amount from about 0 to about 23 g; ascorbic acid in an amount from about 0 to about 12 g; sodium ascorbate in an amount from about 0 to about 12 g, and mixtures of any of the foregoing.

33. The kit of claim 32, wherein the electrolytes and buffers/acids are contained in a single or multiple separate packets with instructions for administration to the patient.

34. The kit of claim 32, wherein the dose of electrolytes and buffers/acids is divided and contained in the containers containing the lactulose doses.

35. The kit of claim 25, further comprising a measuring and/or mixing device.

36. The kit of claim 25, further comprising a patient record for recording the time and/or amount and/or number of doses ingested.

37. The kit of claim 25, which comprises a single container which is a pouch or packet containing from about 180 g to about 220 g lactulose.

38. The kit of claim 25, wherein the kit comprises about 4 containers, each container containing from about 45 g to about 110 g of lactulose in powder form.

* * * * *